United States Patent [19]

Tarasov

[11] 4,401,835

[45] Aug. 30, 1983

[54] METHOD FOR PREPARING SMALL SIZED BENZOYL PEROXIDE CRYSTALS

[75] Inventor: Arthur Tarasov, Upper Montclair, N.J.

[73] Assignee: Warner-Lambert Company, Morris Plains, N.J.

[21] Appl. No.: 303,229

[22] Filed: Sep. 17, 1981

[51] Int. Cl.³ .......................................... C07C 179/06
[52] U.S. Cl. .................................... 568/559; 568/558; 568/562; 252/186.26; 252/410
[58] Field of Search ............... 568/558, 559, 562, 576; 252/186

[56] References Cited

U.S. PATENT DOCUMENTS

| | | | |
|---|---|---|---|
| 2,453,070 | 11/1948 | Hyatt et al. | 568/558 |
| 3,535,422 | 10/1970 | Cox et al. | 424/164 |
| 3,591,540 | 7/1971 | Prashah | 568/559 |
| 3,954,880 | 5/1976 | Nakayama et al. | 568/558 |

Primary Examiner—Werren B. Lone

Attorney, Agent, or Firm—Daniel A. Scola, Jr.; Gary M. Nath

[57] ABSTRACT

A method for the preparation of benzoyl peroxide in crystalline form, which crystals may range in size below 10 microns, comprises forming a first solution of the benzoyl peroxide in a precipitate promoting material, adding the first solution to a second solution comprising an aqueous solution of a dispersant, to precipitate the benzoyl peroxide in the desired crystalline form, and finally recovering the crystalline benzoyl peroxide from the first and second solutions. The precipitate promoting material may be selected from sulfur-containing aliphatic ethers, long-chain aliphatic and araliphatic ethers, ethylene oxide derivatives, and mixtures thereof. The dispersant may be selected from cellulosic derivatives, anionic surfactants, nonionic surfactants, colloidal inorganic materials, and mixtures thereof. The present method may be performed at room temperature and is therefore safe and energy conservative. The resulting benzoyl peroxide crystals are of desirably reduced size, and are particularly well suited for incorporation into commercial cosmetic and pharmaceutical preparations.

50 Claims, 4 Drawing Figures

METHOD FOR PREPARING SMALL SIZED BENZOYL PEROXIDE CRYSTALS

BACKGROUND OF THE INVENTION

1. Field of the Invention

The present invention relates to the preparation of crystalline benzoyl peroxide, and more particularly to the preparation of benzoyl peroxide crystals of reduced size.

2. Description of the Prior Art

Benzoyl peroxide is a well known compound having a broad usage in topical pharmaceutical preparations and toiletries, with particular popularity as the active ingredient in many acne creams and lotions. One of the desired characteristics of such products including benzoyl peroxide, is that the product should have as smooth a texture as possible, to gain greater consumer satisfaction. As benzoyl peroxide is highly insoluble, and is generally held in suspension when included in these products, it has been a prior practice to reduce particle size of the benzoyl peroxide by grinding or the like to particles ranging in size below 20–25 microns. Grinding of benzoyl peroxide is performed, for example, during the preparation of an emulsion or gel product, wherein the benzoyl peroxide suspended in a suitable vehicle, such as water, is placed in a colloid mill and ground at a gap of, for example, 0.005 inches–0.003 inches. Similarly, the particle size of the suspension of benzoyl peroxide may be mechanically reduced by treatment with a roller mill. While these techniques will reduce fine crystals to an acceptable size range, they are incapable of reducing the size of larger crystals.

In addition to the esthetic factors mentioned above, the reduction in the particle size of the benzoyl peroxide increases the effective surface area and thereby maximizes its medicinal efficacy, so that smaller amounts of the material may be necessary to provide a given level of therapeutic effect. The reduction of benzoyl peroxide crystals by grinding or milling, however, is undesirable as it is energy consumptive and potentially dangerous, as the benzoyl peroxide is sensitive to heat friction and percussion, and may cause explosions to occur during grinding.

A need, therefore, exists for a safer, more effective and controllable, and less energy consumptive way for reducing the size of benzoyl peroxide crystals.

SUMMARY OF THE INVENTION

In accordance with the present invention, a method for preparing benzoyl peroxide in crystalline form comprises forming a first solution with said benzoyl peroxide in a precipitate promoting material that is water miscible and nonreactive with the benzoyl peroxide. The first solution is then added to a second solution comprising an aqueous solution of dispersant to form a suspension of reduced size benzoyl peroxide crystals. The first solution is preferably added to the second solution slowly and under agitation, such as continuous stirring.

The benzoyl peroxide is thereafter recovered in crystal form from the mixture, and may be stored or incorporated into cosmetic or pharmaceutical preparations.

Suitable precipitate promoting materials may be selected from the group consisting of sulfur-containing aliphatic ethers, long-chain aliphatic and araliphatic ethers, ethylene oxide derivatives, and mixtures thereof. The benzoyl peroxide is added to the precipitate promoting solvent in an amount ranging up to its solubility limit, and preferably in an amount of up to about 15% by weight of the precipitate promoting material.

The second solution may contain the dispersant in amounts up to about 5% by weight, and preferably in amounts ranging from about 0.1% to about 5% by weight.

The method of the present invention results in the formation of benzoyl peroxide crystals having particle sizes advantageously ranging up to about 10 microns. Crystal size may be controlled by varying the concentration of benzoyl peroxide initially added to the dispersing solution, and/or by careful selection of the solvents or mixtures thereof.

The present method offers the advantages of ease and uniformity of crystal formation, and reduces the risk of explosion present in the practice of the mechanical processes of crystal reduction. Further, the present method may be performed at room temperature so that energy expenditure and product instability caused by elevated temperatures is avoided.

Accordingly, it is a principal object of the present invention to provide a method for preparing benzoyl peroxide crystals of reduced size suitable for pharmaceutical and cosmetic applications.

It is a further object of the present invention to provide a method as aforesaid which reduces the dangers associated with mechanical impact of the benzoyl peroxide crystals.

It is a yet further object of the present invention to provide a method as aforesaid which yields reduced-size crystals of greater uniformity.

It is a yet further object of the present invention to provide a method as aforesaid which requires less time and energy to practice.

Other objects and advantages will become apparent to those skilled in the art from a review of the ensuing description which proceeds with reference to the following illustrative drawings.

DETAILED DESCRIPTION

Figure 1:
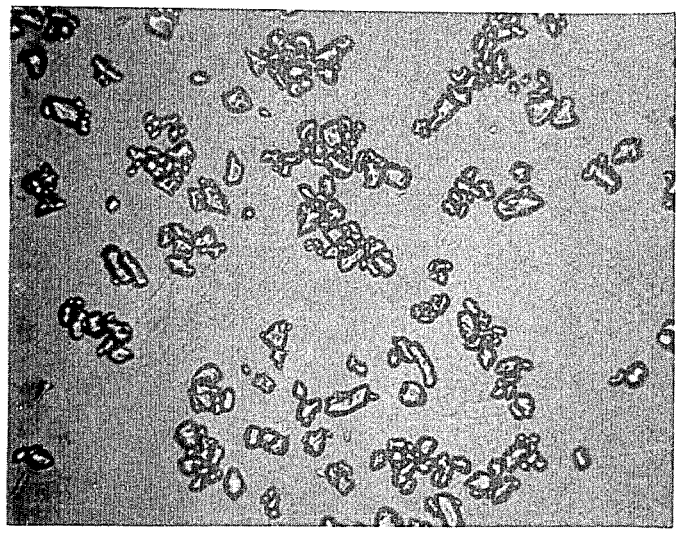
FIGS. 1 and 2 represent photomicrographs at 500× magnification illustrating benzoyl peroxide crystals prepared in accordance with the prior art.

The present invention comprises a method for preparing benzoyl peroxide in crystalline form with crystals of reduced size.

Benzoyl peroxide is available in a variety of states, depending upon desired end use. Thus, benzoyl peroxide may be prepared with a purity of 98%, or lower, and may be in hydrated form, or prepared as a non-aqueous flour, with a suitable innocuous carrier such as starch. Those forms of benzoyl peroxide having little or no water are suitable as starting materials for the present method.

The first step of the present method comprises preparing a first solution comprising benzoyl peroxide granules obtained in 98% purity, and a precipitate promoting material.

The precipitate promoting material may be selected from the group consisting of sulfur-containing aliphatic ethers, long-chain aliphatic and araliphatic ethers, ethylene oxide derivatives, and mixtures thereof.

Preferably, the precipitate promoting material is selected from the group consisting of the dimethyl ether of 1,4:3,6-dianhydrosorbitol, tetrahydrothiophene-1,1-dioxide, dimethyl sulfoxide, ethylene glycol diacetate, cellosolve acetate, propylene carbonate, and mixtures thereof. In the preferred embodiment, the precipitate promoting material is selected from the dimethyl ether of 1,4:3,6-dianhydrosorbitol and tetrahydrothiophene-1,1-dioxide.

The preparation of the first solution proceeds by the addition of the benzoyl peroxide powder to a quantity of the precipitate promoting material. The amount of the benzoyl peroxide added to the precipitate promoting material may range up to the solubility limit of the benzoyl peroxide in said material. Preferably, the benzoyl peroxide may be added in an amount ranging up to about 15% by weight of the precipitate promoting material. and in a preferred embodiment, the benzoyl peroxide may be added in an amount ranging from about 3% to about 10% by weight of the precipitate promoting material.

In the practice of the present invention, it has been noted that the concentration of the benzoyl peroxide in the respective solutions, affects the size of the crystals formed thereby. The production of finer sized crystals may be desirable in certain applications, where, as mentioned earlier, optimal effectiveness of benzoyl peroxide is related to surface area per unit weight of the benzoyl peroxide.

After the preparation of the first solution, the present method proceeds with the addition of the first solution to a second solution, wherein the benzoyl peroxide precipitates as a fine crystalline dispersion. The second solution comprises an aqueous solution of a dispersant which is nonreactive with respect to benzoyl peroxide, and is nontoxic and therefore safe for topical application, in the instance where the benzoyl peroxide crystals are to be incorporated into pharmaceutical or cosmetic preparations. The dispersant may be selected from cellulosic derivatives and certain surfactants, including both anionic surfactants and nonionic surfactants, as well as certain inorganic colloidal materials. The cellulosic derivatives may comprise cellulose ethers and cellulose esters; cellulose ethers may be selected from carboxymethyl cellulose, hydroxyethyl cellulose and the like.

Those anionic surfactants useful herein include the higher alkyl phosphates, sulfates, and sulfonates, such as sodium lauryl ether sulfate, sodium lauryl sulfate, sodium octyl sulfate, triethanolamine tetradecyl sulfate; diamyl sodium sulfosuccinate, di-isobutyl sodium sulfosuccinate, dioctyl sodium phosphate, and others.

Suitable nonionic surfactants include long-chain aliphatic ethers, and long-chain ethoxylated ethers, including materials such as alkylarylpolyethoxyethanol, polyoxyethylene sorbitan monopalmitate, polyoxyethylene sorbitan monolaurate, alkylphenoxypolyethoxy ethanol, iso-octylphenoxyethoxy ethanol and the like. The dispersant may also be a colloidal inorganic material such as a polysilicate, and, more particularly, may comprise colloidal magnesium silicate.

The materials listed above are exemplary of the broad classes of compounds useful as the dispersant in the present invention. It is to be understood, however, that the invention is not limited to the compounds recited above, but rather embraces those broad classes of materials both nontoxic and nonreactive, that are generally stated as suitable for use as the dispersant.

The second solution is preferably prepared with a quantity of dispersants ranging up to about 5.0% by weight. Preferably, the dispersant is present in an amount ranging from about 0.1% to about 5.0% by weight. The presence of the dispersant within this range assures sufficient separation of the benzoyl peroxide crystals upon their formation. It is important that the benzoyl peroxide crystals be dispersed and maintained apart from each other at this stage of the present method, as crystals have a tendency to agglomerate and to form larger structures during their formation. Accordingly, the provision of the dispersants of the present invention within the aforementioned limits advantageously encourages the formation of the crystals when the first solution is added thereto, and further maintains the separation of the crystals thus formed, to assure the maintenance of the reduced size of the desired crystalline end product.

The addition of the first solution to the second solution is preferably conducted slowly and with constant agitation, to assure the formation of the fine crystalline product. Specifically, the first solution is added as a slow stream to the second solution, while vigorous agitation of the second solution is constantly maintained. Agitation may be maintained by stirring, or by other commercial means in the instance where full plant production utilizing the present method is instituted.

It is also naturally desirable that the addition of the first solution to the second solution be performed with apparatus generally inert and nonreactive with the reactants. Specifically, the agitating device or stirrer is preferably composed of 316 stainless steel or ceramic, to assure inertness with respect to the reactants.

One of the advantages of the present invention, is that the foregoing sequence of steps need not be performed at elevated temperatures, and is advantageously performed in its entirety at room temperature. Thus, the present method is economical as it may be performed without the expenditure of substantial heat energy. In addition to the economy of room temperature operation, the present method substantially reduces the danger associated with the prior art processing of benzoyl peroxide, generally attributable to its heat and friction sensitivity and explosiveness.

After the formation of the fine crystalline benzoyl peroxide is complete, the crystalline end product may be recovered from the resulting dispersion by one of many well known separation techniques. Thus, the dispersion may be centrifuged to segregate the crystalline end product, or the dispersion may be filtered to effect similar separation of the crystals. Both techniques are well known, and are merely illustrative of separation techniques useful in accordance with the present invention.

After separation of the crystalline end product, it is desirably further separated from the dispersion medium, to assure its purity. Particularly in the instance where the product is to be incorporated in commercial preparations such as cosmetic and pharmaceutical compositions, it is important that the crystals be free from adsorbed solvent or dispersant remaining from the earlier steps of the present method. Thus, the crystals may be further treated by washing with water, such washing conducted at least one time, and, when desirable, a series of repetitive washings of the crystals may be conducted.

After the crystals have been finally treated such as by washing, they may be either directly incorporated into commercial preparations such as mentioned above, or may be appropriately contained and stored for later use. At this stage, the crystals maintain their individual integrity, and even in the instance where they are recovered as a "cake", the cake can be later dispersed and will yield crystals of desired size and uniformity.

The present method is particularly useful in the instance where the commercial preparations such as topical pharmaceutical and cosmetic compositions are being prepared. In such instance, the present invention may be conducted in an ongoing commercial manner to provide a constant supply of benzoyl peroxide crystals of uniform and reduced size for direct incorporation into pharmaceutical and cosmetic compositions.

As noted earlier, crystals prepared in accordance with the present invention are desirably reduced in crystal size, and provide greater uniformity than was capable of achievement by the processes of the prior art. The following examples, including comparative Examples I and II are provided below with reference to accompany photomicrographs, to illustrate the advantages of the present invention.

EXAMPLES I & II

Two compositions consecutively identified as above, were prepared with benzoyl peroxide crystals prepared by known procedures. In each composition, the benzoyl peroxide starting materials comprised relatively coarse granules, that were reduced in size by first dispersing the granules in a chemically inert liquid medium, such as a suitable emollient or water, and thereafter subjecting the resulting dispersions to the action of a roller mill. The dispersions were milled by one or more consecutive passes through the roller mill, to reduce the majority of the benzoyl peroxide granules to a size smaller than about 0.25 mm.

After milling was completed, the resulting slurries were formulated into the respective compositions, and were combined with other ingredients appropriate for the preparation of acne medications. The compositions of Examples I and II may be prepared in accordance with prior art procedures, such as disclosed in U.S. Pat. No. 3,535,422, the disclosure of which is incorporated herein by reference.

After their preparation, samples of the respective compositions were placed on slides, and photomicrographs were made at 500× magnification. The photomicrographs in FIGS. 1 and 2, correspond respectively, to the compositions of Examples I and II herein.

EXAMPLE III

A composition was prepared in accordance with the present invention. Benzoyl peroxide powder was added to a quantity of tetrahydrothiophene-1,1-dioxide, and the resulting solution was thereafter added to a dilute solution of sodium lauryl ether sulfate. This dispersion was thereafter maintained, and a photomicrograph at 500× magnification was made of a sample. The remaining dispersion was permitted to sit for five days, after which it was restirred, and minimal agglomeration was then noted.

EXAMPLE IV

A further example of the present invention was prepared wherein benzoyl peroxide was added to the dimethyl ether of 1,4:3,6-dianhydrosorbitol, and the resulting solution was thereafter added to a second solution containing a dispersant comprising a combination of cellulosic derivative and a nonionic surface active agent. The crystalline precipitate thus formed was maintained in dispersion, and a photomicrograph was taken of a sample thereof, and is set forth herein as FIG. 4.

Figure 2:
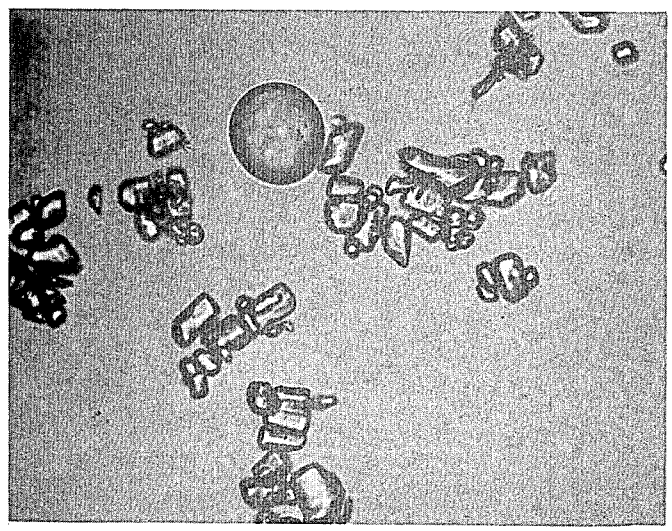
Figure 3:
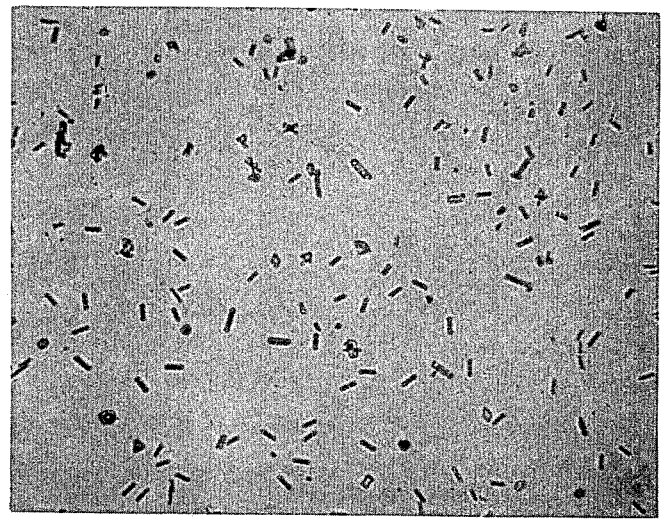
FIGS. 3 and 4 represent photomicrographs taken at 500× magnification, illustrating benzoyl peroxide crystals prepared in accordance with the present invention.
Figure 4:
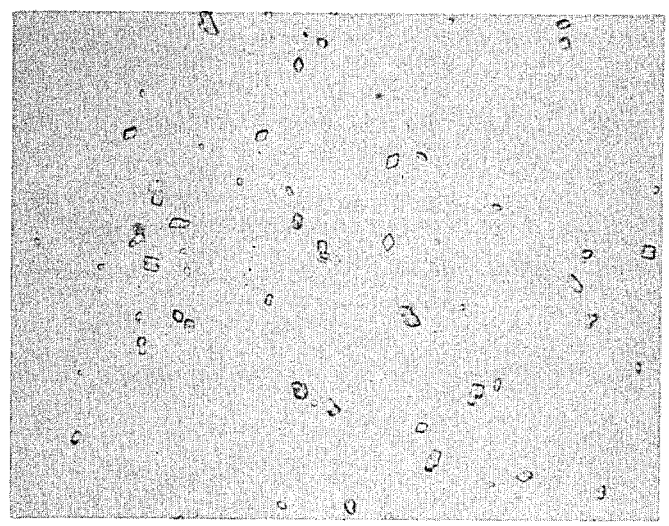

Referring now to the Figures for purposes of comparison, it is clear that FIGS. 1 and 2, representing the prior art disclose much larger and coarser sized benzoyl peroxide crystals than those shown in FIGS. 3 and 4, representing the present invention. Moreover, crystals illustrated in the Examples representing the present invention are more uniform as well as finer, by contrast with the irregularly shaped and far more coarse crystals shown in FIGS. 1 and 2.

From the foregoing observations, it may be concluded that the practice of the present invention results in the formation of a more uniform, and finer sized benzoyl peroxide crystal than those apparently obtainable by the prior art. Moreover, the practical advantages of the present invention, namely those of speed, safety and economy of crystal formation, serve to further distinguish the present invention favorably from that of the prior art.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A method for preparing benzoyl peroxide in crystalline form with crystals having a size ranging up to about 10 microns, comprising:
    forming a first solution comprising said benzoyl peroxide and a precipitate promoting material selected from sulfur-containing aliphatic ethers, long-chain aliphatic and araliphatic esters, ethylene oxide derivatives, and mixtures thereof;
    adding said first solution to a second solution comprising an aqueous solution of a nontoxic and nonreactive dispersant, said dispersant selected from cellulosic derivatives, anionic surfactants, nonionic surfactants, inorganic colloidal materials, and mixtures thereof; and
    recovering said benzoyl peroxide in said crystalline form.

2. A method for preparing benzoyl peroxide in crystalline form with crystals having a size ranging up to about 10 microns, comprising:
    forming a first solution comprising said benzoyl peroxide and a precipitate promoting material selected from the dimethyl ether of 1,4:3,6-dianhydrosorbitol, tetrahydrothiophene-1,1-dioxide, dimethyl sulfoxide, ethylene glycol diacetate, cellosolve acetate, propylene carbonate, and mixtures thereof;
    adding said first solution to a second solution comprising an aqueous solution of a nontoxic and nonreactive dispersant, said dispersant selected from cellulose ethers, cellulose esters, long-chain aliphatic ethers, long-chain ethoxylated ethers, higher alkyl phosphates, higher alkyl sulfates, higher alkyl sulfonates, colloidal polysilicates, and mixtures thereof; and recovering said benzoyl peroxide in said crystalline form.

3. The method of claim 2 wherein said precipitate promoting material is selected from the dimethyl ether of 1,4:3,6-dianhydrosorbitol and tetrahydrothiophene-1,1-dioxide.

4. The method of claim 2 wherein said dispersant comprises a mixture of a cellulose ether and a long-chain ethoxylated ether.

5. The method of claim 2 wherein said dispersant is selected from carboxymethyl cellulose, hydroxyethyl cellulose; sodium lauryl ether sulfate, sodium lauryl sulfate, sodium octyl sulfate, triethanolamine tetradecyl sulfate, diamyl sodium sulfosuccinate, di-isobutyl sodium sulfosuccinate, dioctyl sodium phosphate; alkylarylpolyethoxyethanol, polyoxyethylene sorbitan monopalmitate, polyoxyethylene sorbitan monolaurate, alkylphenoxypolyethoxy ethanol, iso-octylphenoxyethoxy ethanol, and mixtures thereof.

6. The method of claim 5 wherein said dispersant is selected from carboxymethyl cellulose, hydroxyethyl cellulose, alkylarylpolyethoxyethanol, sodium lauryl ether sulfate, and mixtures thereof.

7. The method of claim 6 wherein said dispersant comprises carboxymethyl cellulose.

8. The method of claim 6 wherein said dispersant comprises a mixture of hydroxyethyl cellulose and alkylarylpolyethoxy ethanol.

9. The method of claim 6 wherein said dispersant comprises sodium lauryl ether sulfate.

10. The method of claim 2 wherein said colloidal polysilicate comprises colloidal magnesium silicate.

11. The method of claims 1-9 or 10 wherein said benzoyl peroxide is present in said first solution in an amount ranging up to its solubility limit in said precipitate promoting material.

12. The method of claim 11 wherein said benzoyl peroxide is present in said first solution in an amount of up to about 15% by weight of said precipitate forming material.

13. The method of claim 12 wherein said benzoyl peroxide is present in said first solution in an amount of from about 3.0% to about 10% by weight of said precipitate forming material.

14. The method of claims 1-9 or 10 wherein said dispersant is present in an amount of up to about 5.0% by weight.

15. The method of claim 14 wherein said dispersant is present in an amount of from 0.1% to 5.0% by weight.

16. The method of claims 1-9 or 10 wherein said first solution is prepared by the addition of said benzoyl peroxide to said precipitate promoting material slowly and under agitation.

17. The method of claim 11 wherein said first solution is prepared by the addition of said benzoyl peroxide to said precipitate promoting material slowly and under agitation.

18. The method of claim 12 wherein said first solution is prepared by the addition of said benzoyl peroxide to said precipitate promoting material slowly and under agitation.

19. The method of claim 13 wherein said first solution is prepared by the addition of said benzoyl peroxide to said precipitate promoting material slowly and under agitation.

20. The method of claim 14 wherein said first solution is prepared by the addition of said benzoyl peroxide to said precipitate promoting material slowly and under agitation.

21. The method of claim 15 wherein said first solution is prepared by the addition of said benzoyl peroxide to said precipitate promoting material slowly and under agitation.

22. The method of claims 1-9 or 10 wherein said benzoyl peroxide is recovered by separation from said solution.

23. The method of claim 11 wherein said benzoyl peroxide is recovered by separation from said solution.

24. The method of claim 12 wherein said benzoyl peroxide is recovered by separation from said solution.

25. The method of claim 13 wherein said benzoyl peroxide is recovered by separation from said solution.

26. The method of claim 14 wherein said benzoyl peroxide is recovered by separation from said solution.

27. The method of claim 15 wherein said benzoyl peroxide is recovered by separation from said solution.

28. The method of claim 16 wherein said benzoyl peroxide is recovered by separation from said solution.

29. The method of claim 17 wherein said benzoyl peroxide is recovered by separation from said solution.

30. The method of claim 18 wherein said benzoyl peroxide is recovered by separation from said solution.

31. The method of claim 19 wherein said benzoyl peroxide is recovered by separation from said solution.

32. The method of claim 20 wherein said benzoyl peroxide is recovered by separation from said solution.

33. The method of claim 21 wherein said benzoyl peroxide is recovered by separation from said solution.

34. The method of claim 22 wherein, after said separation, said benzoyl peroxide is washed at least one time.

35. The method of claim 23 wherein, after said separation, said benzoyl peroxide is washed at least one time.

36. The method of claim 24 wherein, after said separation, said benzoyl peroxide is washed at least one time.

37. The method of claim 25 wherein, after said separation, said benzoyl peroxide is washed at least one time.

38. The method of claim 26 wherein, after said separation, said benzoyl peroxide is washed at least one time.

39. The method of claim 27 wherein, after said separation, said benzoyl peroxide is washed at least one time.

40. The method of claim 28 wherein, after said separation, said benzoyl peroxide is washed at least one time.

41. The method of claim 29 wherein, after said separation, said benzoyl peroxide is washed at least one time.

42. The method of claim 30 wherein, after said separation, said benzoyl peroxide is washed at least one time.

43. The method of claim 31 wherein, after said separation, said benzoyl peroxide is washed at least one time.

44. The method of claim 32 wherein, after said separation, said benzoyl peroxide is washed at least one time.

45. The method of claim 33 wherein, after said separation, said benzoyl peroxide is washed at least one time.

46. The method of claims 1-9 or 10 wherein said method is conducted at room temperature.

47. The method of claim 11 wherein said method is conducted at room temperature.

48. The method of claim 16 wherein said method is conducted at room temperature.

49. The method of claim 22 wherein said method is conducted at room temperature.

50. The method of claim 34 wherein said method is conducted at room temperature.

* * * * *